United States Patent
Carry et al.

(10) Patent No.: US 12,076,516 B1
(45) Date of Patent: Sep. 3, 2024

(54) ADJUSTABLE LENGTH TELESCOPING DILATOR

(71) Applicant: CG Medical LLC, Danville, PA (US)

(72) Inventors: Brendan James Carry, Danville, PA (US); Evan Gajkowski, Catawissa, PA (US); Dominik Beer, Lewisburg, PA (US)

(73) Assignee: CG Medical LLC, Danville, PA (US)

( * ) Notice: Subject to any disclaimer, the term of this patent is extended or adjusted under 35 U.S.C. 154(b) by 0 days.

(21) Appl. No.: 18/466,198

(22) Filed: Sep. 13, 2023

(51) Int. Cl.
*A61M 29/00* (2006.01)
*A61M 25/09* (2006.01)

(52) U.S. Cl.
CPC ............ *A61M 29/00* (2013.01); *A61M 25/09* (2013.01); *A61M 2210/12* (2013.01)

(58) Field of Classification Search
CPC .. A61M 29/00; A61M 25/09; A61M 2210/12; A61B 2017/347; A61B 2017/00991; A61B 17/3417; A61F 2250/0065
See application file for complete search history.

(56) References Cited

U.S. PATENT DOCUMENTS

| | | | | |
|---|---|---|---|---|
| 4,862,891 A | * | 9/1989 | Smith | A61M 29/00 606/191 |
| 7,811,303 B2 | * | 10/2010 | Fallin | A61B 17/3417 606/191 |
| 2006/0210432 A1 | * | 9/2006 | Victor | G01N 35/00029 422/63 |
| 2009/0149857 A1 | * | 6/2009 | Culbert | A61B 1/0684 606/191 |
| 2016/0206347 A1 | * | 7/2016 | Bar | A61M 29/00 |
| 2018/0126121 A1 | * | 5/2018 | Mauch | A61F 2/2427 |
| 2021/0228198 A1 | * | 7/2021 | LaPierre | A61B 17/3421 |

* cited by examiner

*Primary Examiner* — Katherine M Rodjom
(74) *Attorney, Agent, or Firm* — Levine Bagade Han LLP

(57) ABSTRACT

Disclosed herein are systems and methods for sequentially dilating a vessel, where a guidewire extends into the vessel through a tissue opening in a tissue surface. The method can comprise advancing a dilator assembly over a portion of the guidewire that is exterior to the tissue opening; extending a first dilator segment from the dilator assembly; advancing at least the first dilator segment into the tissue opening to dilate the vessel while the first dilator segment remains extended from the dilator assembly; extending a second dilator segment from the dilator assembly, where the first dilator segment remains coupled to the second dilator segment and partially extends from the second dilator segment; advancing the first dilator segment and the second dilator segment into the tissue opening to further sequentially dilate the vessel while the second dilator segment remains extended from the dilator assembly.

10 Claims, 13 Drawing Sheets

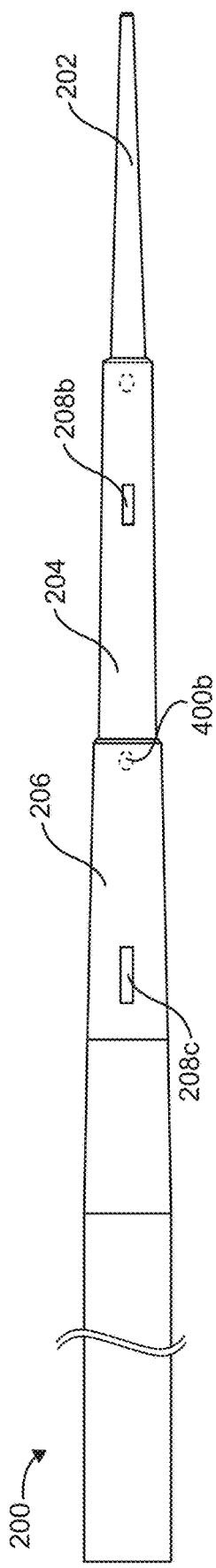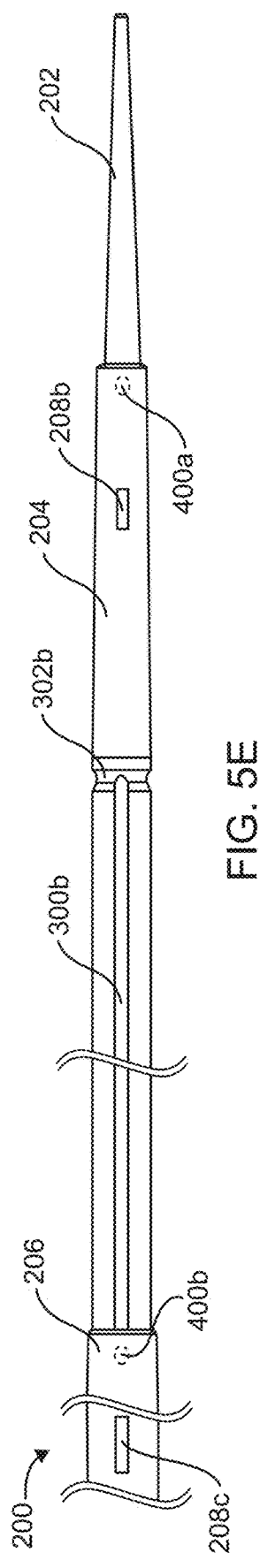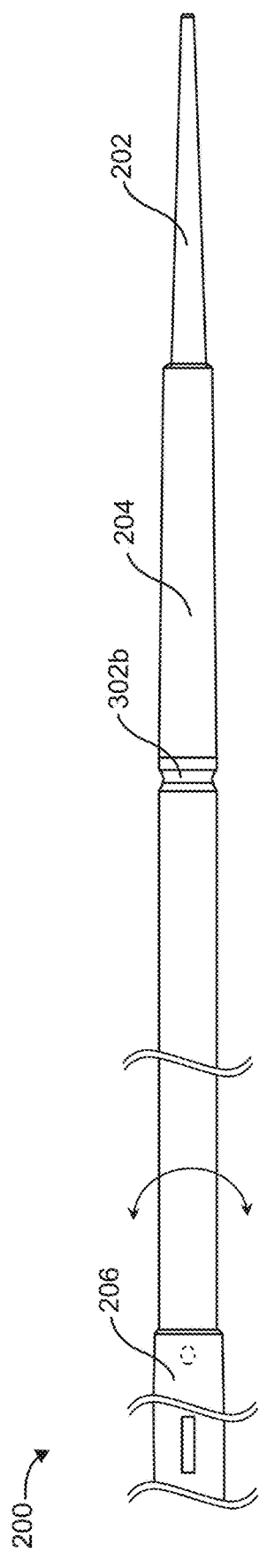
FIG. 5D
FIG. 5E
FIG. 5F

ADJUSTABLE LENGTH TELESCOPING DILATOR

FIELD OF TECHNOLOGY

The present disclosure relates generally to the field of dilating a blood vessel multiple times, and, more specifically, to systems and devices for accessing the femoral artery or the femoral vein.

BACKGROUND

Safe and quick vascular access during interventional procedures is paramount for patient safety and outcomes. The typical catheterization procedure during an interventional vascular procedure involves a hollow needle, a guide wire, and dilators of increasing diameter typically ranging from 8-30 French. The starting French size is determined by the physician before the catheterization process begins and is based on the estimated size of the patient's vessels. First, the needle is positioned within the vessel, then a guidewire is advanced into the needle such that the distal portion of the guidewire is in the vessel and a proximal portion of the guidewire remains outside the patient. The needle is then removed, leaving the guidewire within the vessel. Then, a dilator is advanced over the guidewire to dilate the tissue opening and vessel. This dilator is then removed, and a dilator with a slightly larger diameter is reintroduced over the wire. The removal of the dilator and insertion of a larger dilator can be repeated five to eight times until the required diameter (French size) determined by the physician is inserted into the patient. This process is similar to many vascular interventions but is especially tedious and time-consuming, which can present problems when the dilation procedure must be performed quickly. For example, in venous arterial extracorporeal membrane oxygenation (VA-ECMO) procedures, blood is pumped outside of the body to a heart-lung machine that removes carbon dioxide and sends oxygen-filled blood back to tissues in the body. Blood is removed from the venous circulation of the body, is oxygenated, then pumped back into the arterial circulation. VA-ECMO is required in the setting of cardiogenic shock. In VV-ECMO, blood is removed from the venous circulation, oxygenated, then pumped back into the venous circulation, and is used in the setting of primary lung failure where cardiac output is maintained and circulatory support is not required. Patients are critically ill and often times are nearing or have sustained cardiopulmonary arrest. Therefore, it is important to prepare the patient for the ECMO procedure as quickly as possible to reestablish oxygenation to the vital organs and tissues. VA-ECMO as well as VV-ECMO procedures require placement of large venous and arterial cannulas (in the case of VA-ECMO) and therefore require sequential dilation of the vessel.

With all catheterization procedures, a multi-step dilation process is typically used. Three catheterization techniques currently exist to prepare a patient for ECMO: the Seldinger technique, the open cut-down technique, and the end-to-side graft technique. The Seldinger technique is a percutaneous technique performed in the patient's room where the femoral artery is punctured with a hollow needle and a guidewire is inserted to allow catheterization. This procedure can occur bedside with local anesthetic and has been shown to have the fewest complications since it is minimally invasive. However, this technique was developed in 1953 and has not been improved since. The open cutdown technique is a surgical procedure to access the femoral artery or vein. It must be performed in a surgical setting with the artery or vein surgically opened and exposed before catheterization. Accordingly, this procedure has a higher incidence of infection around the incision and requires more time than the Seldinger technique. The end-to-side graft technique involves attaching a Dacron graft (synthetic polyester material used to replace natural body tissue) to the femoral artery before catheterization via the Seldinger technique. This technique has not been widely adopted, as it has a higher risk of infection than the standard Seldinger technique and is not as cost-effective.

Other issues can arise with conventional techniques. Guidewires can flop back and forth from repeated advancement of dilators over the guidewire, making the procedure more cumbersome, less sterile (increasing the risk of subsequent infection), and potentially slower. In addition, repeated insertion of dilators can be difficult if there is only one user, as the user must use their hand to suppress blood flow from an already partially dilated arteriotomy or venotomy, leaving the user with only one free hand to prepare and advance a subsequent dilator. Even further, repeated withdrawal and insertion of dilators can lead to unwanted blood loss out of the body, into the surrounding tissues, and into the vessel wall (pseudoaneurysm).

Accordingly, there remains a need for new devices and methods to address radial expansion of vessels and tissue for medical procedures, particularly for intravascular catheters and dilators that benefit from timeliness of the procedure. Specific to ECMO procedures, dilation must be performed as quickly as possible to oxygenate the brain and vital organs. ECMO procedures may require insertions in both femoral veins (VV) or femoral vein and artery (VA), which doubles the amount of sequential dilation required. This adds even more time to the overall procedure and can result in potential harm to the patient if oxygenated blood flow is not restored expeditiously.

Therefore, a solution is needed for sequential dilation to fully dilate a vessel with one device to reduce procedure time and to limit the number of foreign objects passing over the guidewire and entering the body. Such methods and devices may improve the patient's likelihood of recovery by restoring adequate oxygenation to the tissues (either with VV-ECMO or VA-ECMO) and decreasing the risk of infection.

SUMMARY

Disclosed are systems, devices, and methods for sequentially dilating a vessel. The method can comprise advancing a dilator assembly over a portion of a guidewire that is exterior to the tissue opening; positioning the dilator assembly over the guidewire and towards the tissue surface while the dilator assembly is in a compact configuration; extending a first dilator segment from the dilator assembly; advancing at least the first dilator segment into the tissue opening to dilate the vessel while the first dilator segment remains extended from the dilator assembly; withdrawing the first dilator segment from the tissue opening and retracting the first dilator segment into the dilator assembly; extending a second dilator segment from the dilator assembly, where the first dilator segment remains coupled to the second dilator segment and partially extends from the second dilator segment; advancing the first dilator segment and the second dilator segment into the tissue opening to further sequentially dilate the vessel while the second dilator segment remains extended from the dilator assembly; withdrawing the first dilator segment and the second dilator segment from the tissue opening and retracting the second dilator segment into the dilator assembly; and withdrawing the dilator assembly from the guidewire. It is noted that the procedure of sequential dilation can occur without the use of a guidewire.

In some embodiments, the method can comprise locking the dilator assembly via a locking mechanism, wherein the locking mechanism comprises a protrusion on an inner surface of the second dilator and a groove on an outer surface of the first dilator, wherein rotating the second dilator with respect to the first dilator engages the protrusion with the groove to lock the dilator assembly.

In some embodiments, the method can further comprise a plurality of grooves radially spaced apart on the outer surface of the first dilator, wherein the protrusion is configured to engage with any of the plurality of grooves.

In some embodiments, the first dilator segment can fully extend from the second dilator segment.

In some embodiments, the method can further comprise extending a third dilator segment from the dilator assembly, where the first dilator segment and the second dilator segment remains coupled to the third dilator segment and partially extend from the third dilator segment; advancing the third dilator segment, the second dilator segment, and the first dilator segment into the tissue opening to further sequentially dilate the vessel while the third dilator segment remains extended from the dilator assembly; and withdrawing the first dilator segment, the second dilator segment, and the third dilator segment from the tissue opening and retracting the third dilator segment into the dilator assembly.

In some embodiments, the second dilator segment can fully extend from the third dilator segment.

In some embodiments, the method can further comprise a locking mechanism, wherein the locking mechanism comprises a protrusion on an inner surface of the third dilator segment and a groove on an outer surface of the second dilator, wherein rotating the third dilator with respect to the second dilator engages the protrusion of the third dilator with the groove of the second dilator to lock the dilator assembly.

In some embodiments, the method can further comprise wherein the first dilator segment comprises a first alignment marker, the second dilator segment comprises a second alignment marker, wherein the first alignment marker and the second alignment marker are longitudinally aligned when the first dilator segment is axially moveable relative to the second dilator segment.

In some embodiments, the method can further comprise wherein the first alignment marker and the second alignment marker are longitudinally misaligned when the first dilator segment is axially locked relative to the second dilator segment.

In some embodiments, the method can further comprise wherein the first alignment marker and the second alignment marker are longitudinally misaligned when the first dilator segment is rotatable relative to the second dilator segment.

Also disclosed is a sequential dilator assembly for a vessel; wherein the sequential dilator assembly can comprise a first dilator segment at least partially nested in a second dilator segment that is at least partially nested within a third dilator segment, wherein the first dilator segment can be axially moved distally relative to the second dilator segment when nested within the third dilator segment, and where the first dilator segment can be releasably locked with the second dilator segment into a first locked configuration; and where the second dilator segment can be axially moved distally relative to the third dilator segment, and where the second dilator segment can be releasably locked with the third dilator segment into a second locked configuration.

In some embodiments, the assembly can further comprise a groove on an outer surface of the first dilator segment; and a protrusion on an inner surface of the second dilator segment, wherein when the protrusion engages the groove, the second dilator segment is locked with respect to the first dilator segment.

In some embodiments, the assembly can further comprise a plurality of grooves radially spaced apart on the outer surface of the first dilator, wherein the protrusion is configured to engage with any of the plurality of grooves.

In some embodiments, the assembly can further comprise a groove on an outer surface of the second dilator segment and a protrusion on an inner surface of the third dilator segment, wherein when the protrusion of the third dilator segment engages the groove of the second dilator, the third dilator segment is locked with respect to the second dilator segment.

In some embodiments, the first dilator segment can comprise a first alignment marker, the second dilator segment comprises a second alignment marker, wherein the first alignment marker and the second alignment marker are longitudinally aligned when the first dilator segment is axially moveable relative to the second dilator segment.

In some embodiments, the first alignment marker and the second alignment marker can be longitudinally misaligned when the first dilator segment is axially locked relative to the second dilator segment.

In some embodiments, the first alignment marker and the second alignment marker can be longitudinally misaligned when the first dilator segment is rotatable relative to the second dilator segment.

BRIEF DESCRIPTION OF THE DRAWINGS

FIGS. 5D to 5F illustrate side views of movement between the second dilator and the third dilator of the dilator assembly of FIG. 2.

DETAILED DESCRIPTION

Figure 1A:
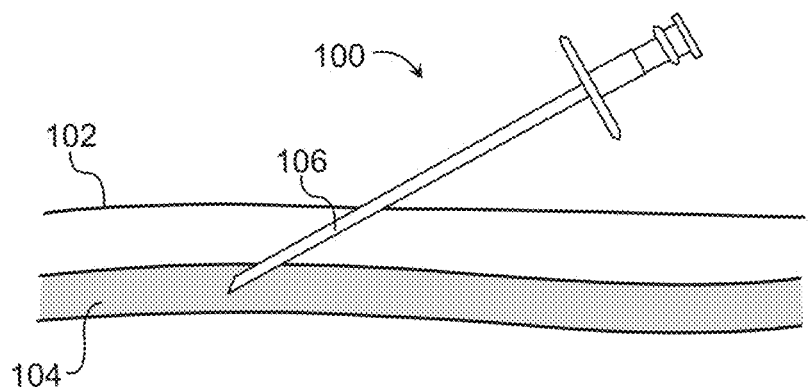
FIGS. 1A to 1C illustrate side views of methods of accessing a vessel with a needle assembly.
Figure 1B:
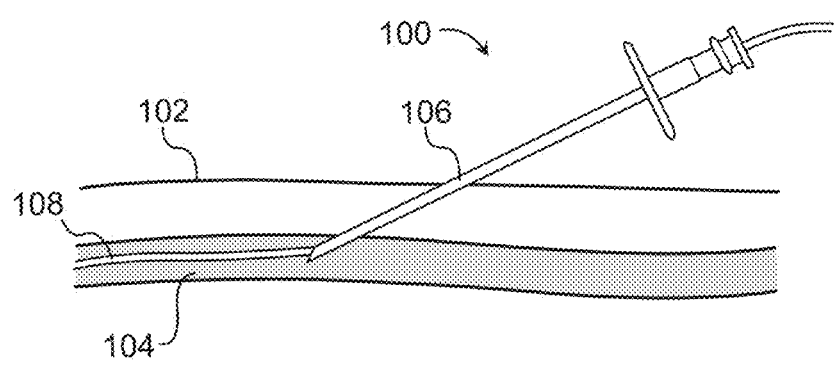
Figure 1C:
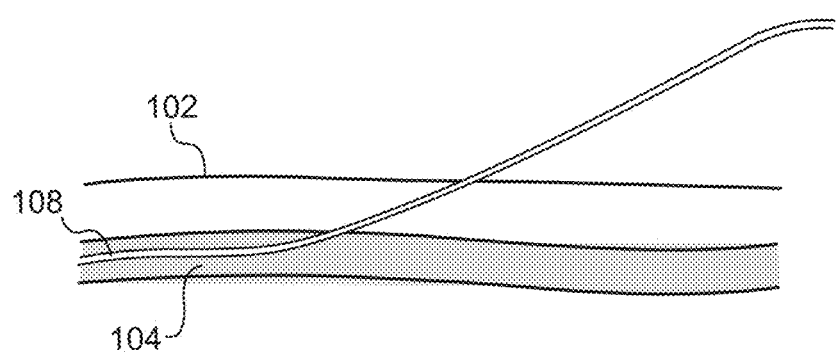

FIGS. 1A to 1C illustrate side views of methods of accessing a vessel with a needle assembly 100. First, a scalpel can be used to cut an incision or tissue opening through the skin 102. A needle assembly 100 can then be then advanced through the incision and to a target vessel 104, as seen in FIG. 1A. A needle 106 can then be advanced into the vessel 104, puncturing the vessel 104, as seen in FIG. 1B. Next, a guidewire 108 advances through the needle assembly 100 into the vessel 104. Once the guidewire 108 is within the vessel 104, the needle assembly 100 is withdrawn. Another incision into the skin 102 can be made as needed.

Figure 1D:
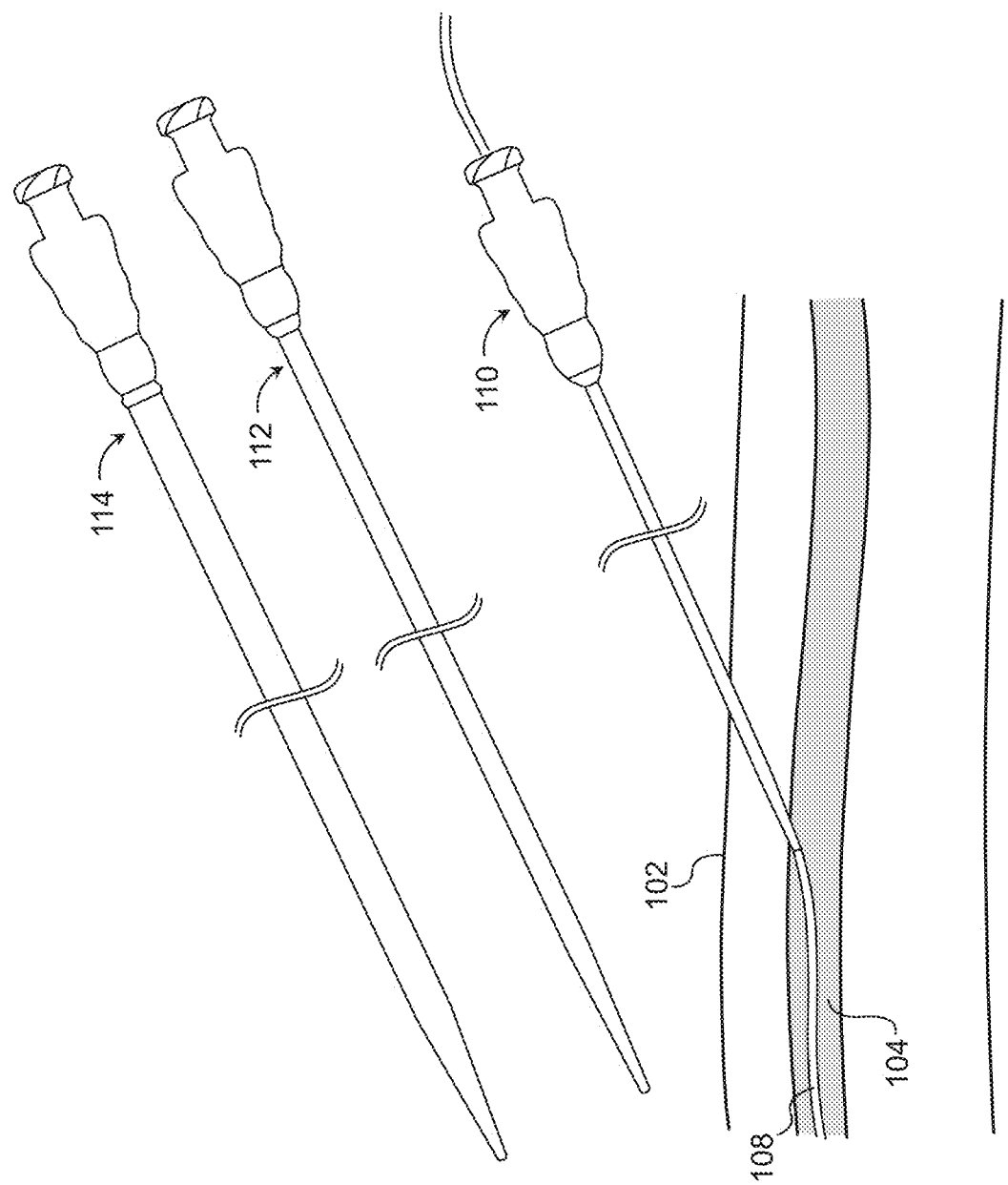
FIG. 1D illustrates a side view of methods of dilating a vessel with a dilator assembly according to the existing prior art.

FIG. 1D illustrates an example of conventional sequential dilation of a vessel with multiple dilators. This conventional dilation uses multiple dilators to incrementally dilate the tissue and vessel to prepare for insertion of another medical device. The dilators are advanced over the guidewire 108, inserted into tissue over the guidewire, and then subsequently withdrawn over guidewire 108. As noted above, the portion of the guidewire 108 exterior to the patient can have a significant length, which presents several problems during a conventional procedure. First, once any vessel is dilated, blood escapes from the insertion site. In the cases of an artery, the blood is pressurized so the caregiver must place pressure on the insertion site to reduce blood loss from the insertion site. Next, the proximal end of the guidewire can move and touch a non-sterile surface. This means that any subsequent dilator that advances over the guidewire is then touching a non-sterile surface, which can lead to an increased risk of infection. Furthermore, the act of withdrawing the dilator over a long guidewire (outside the body) and then advancing a larger dilator over the guidewire can add considerable time to the procedure as noted above.

Figure 2:
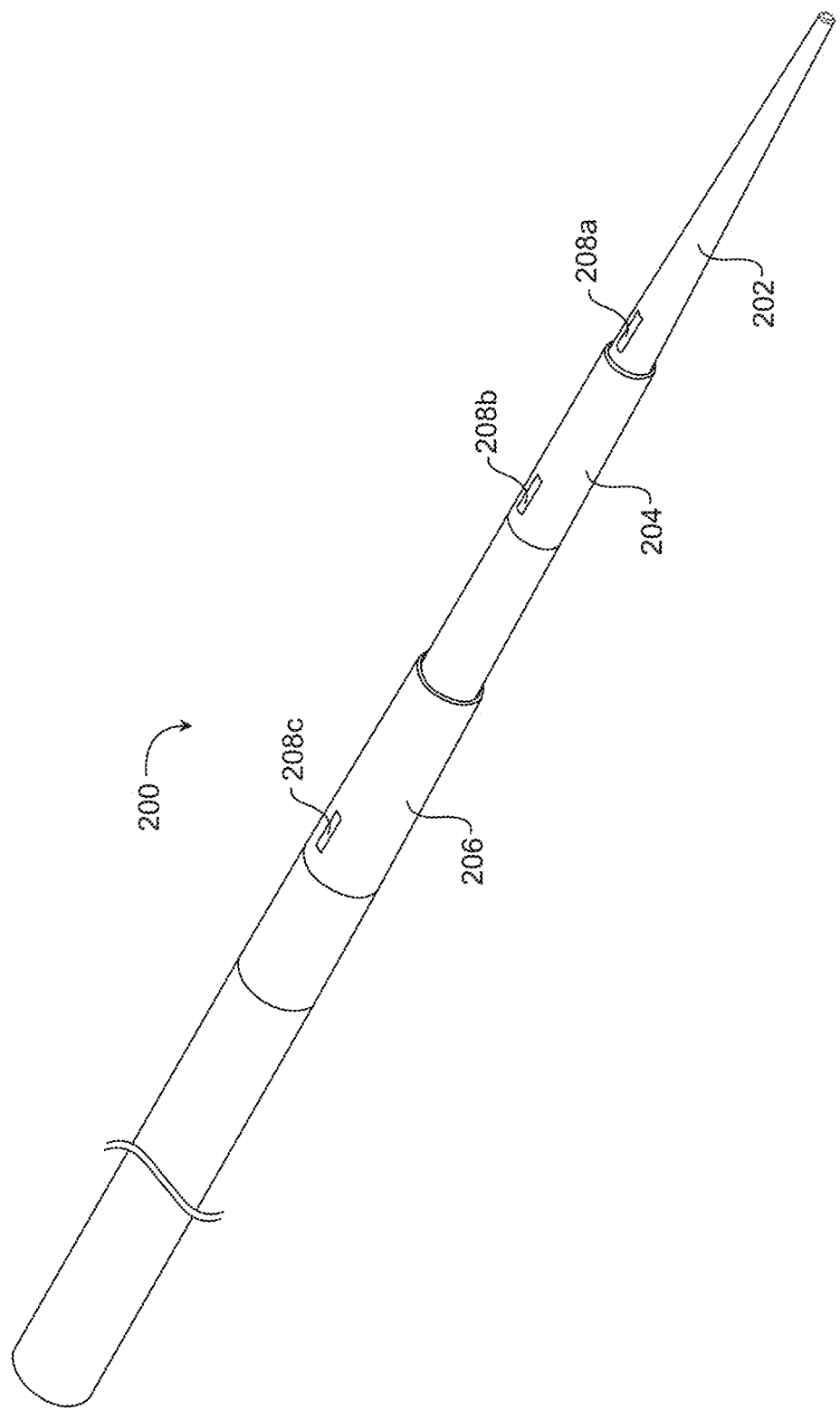
FIG. 2 illustrates a perspective view of a dilator assembly in accordance with the present invention.

FIG. 2 illustrates a perspective view of an example of a novel dilator assembly 200 configured for a sequential dilation procedure without the drawbacks discussed above. The dilator assembly 200 can comprise multiple dilator segments that each have increasing diameters to sequentially dilate a tissue opening. For purposes of illustration, the dilator 200 of FIG. 2 includes a first dilator segment 202, a second dilator segment 204, and a third dilator segment 206 each having a greater diameter. It is understood that any number of dilator segments can be used in a single device under the present disclosure from a minimum of two.

As illustrated, the first dilator segment 202, the second dilator segment 204, and the third dilator segment 206 can each comprise tapering sections between regions. The tapering sections can be longer or shorter in axial length than those illustrated in FIG. 2. In the illustrated variation, the first dilator segment 202 extends concentrically into the second dilator segment 204 and the second dilator segment 204 extends concentrically into the third dilator segment 206. As discussed below, this allows any dilator segment to be exposed/extended such that it can be used for sequential dilation of the tissue.

The first dilator segment 202 can have a maximum diameter between about 13 French and about 16 French (e.g., 16 French). The second dilator segment 204 can have a maximum diameter between about 16 French and about 20 French (e.g., 20 French). The third dilator segment 206 can have a maximum diameter between about 20 French and about 26 French (e.g., 26 French).

In a fully extended configuration, a total length of variations of the dilator assembly 200 can be between about 40 cm to 100 cm (e.g., 86 cm). In a partially collapsed configuration, a total length of the dilator assembly 200 can be between about 35 cm to 70 cm (e.g., 55 cm). In a collapsed configuration, the total length of variations of the dilator assembly 200 can be between about 25 cm to 40 cm (e.g., 30 cm).

The first dilator segment 202, the second dilator segment 204, and the third dilator segment 206 can each comprise an alignment marker 208a, 208b, 208c respectively. The alignment markers 208a, 208b, 208c can be a visually identifiable from an exterior of the assembly 200 such as a detent on an outer surface of the dilator segment. Alternatively, or in combination, the alignment markers 208a, 208b, 208c can be markers that are tactile and/or identifiable via non-invasive imaging (e.g., radiopaque, echogenic, etc.)

Figure 3:
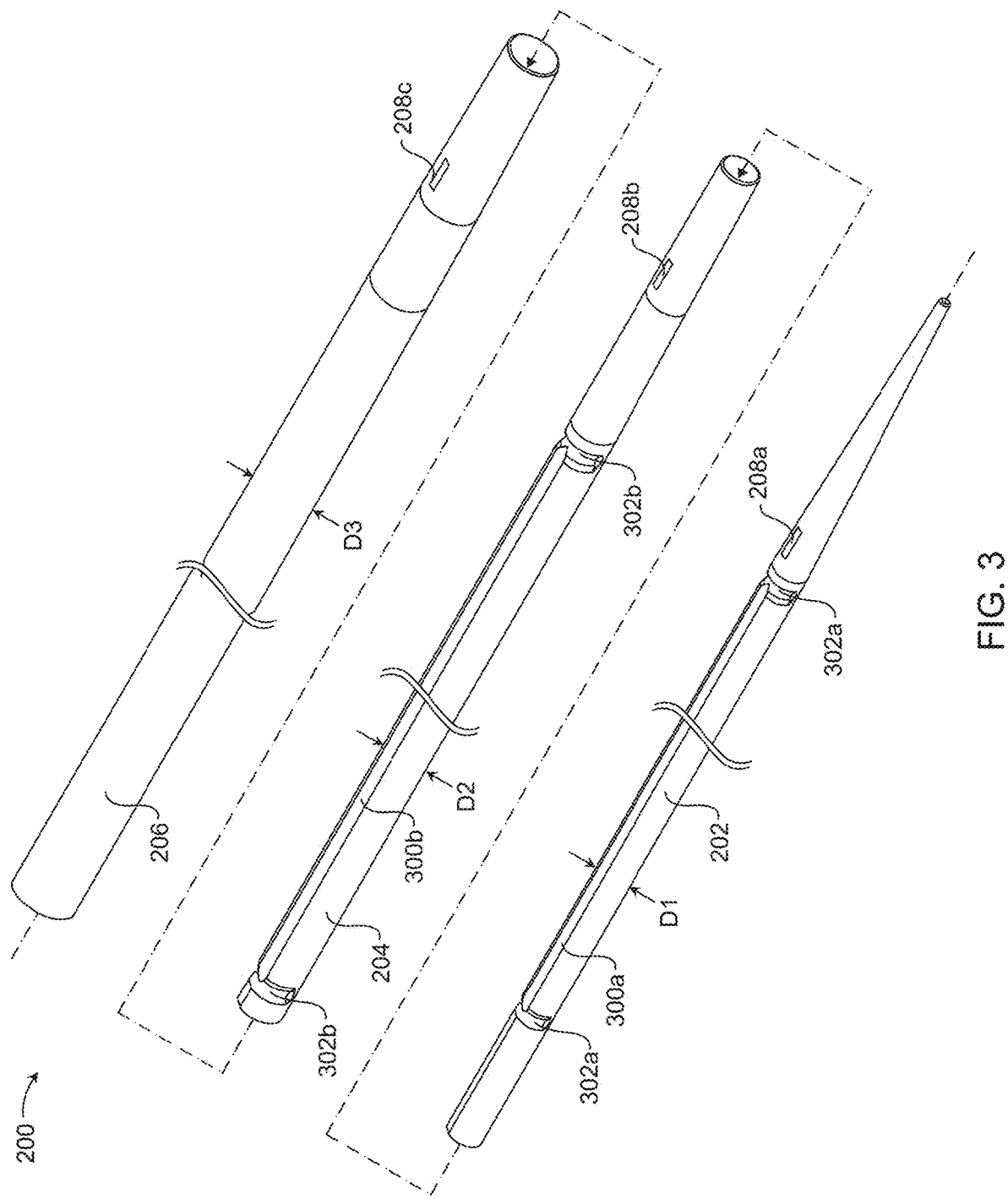
FIG. 3 illustrates an exploded view of the dilator assembly of FIG. 2.

FIG. 3 illustrates an exploded view of the dilator assembly of FIG. 2. It is understood that the features shown in FIG. 3 are for a variation of the sequential dilation assembly 200 disclosed herein. The dilation assembly can have two or more sized dilator segments and can incorporate any locking structure that permits a dilator segment to be extended and then locked relative to the dilator assembly. As shown in the illustrated example, the first dilator segment 202 and the second dilator segment 204 both comprise one or more longitudinal grooves 300a, 300b and one or more circumferential grooves 302a, 302b on an outer surface thereof. In some embodiments, there can be a plurality of longitudinal grooves spaced radially apart on the outer surface. In some embodiments, there can be a circumferential groove 302a, 302b at both a proximal end and a distal end of the dilator segment. The circumferential groove 302a. 302b can extend either partially (e.g., 180 degrees) or fully around the outer surface. As described below, these grooves allow securing dilator segments relative to the dilator assembly 200 for sequential dilation. Again, the dilator segments 202, 204, 206 can each include a tapered distal section to facilitate dilation, the tapered segment can be adjacent to a constant diameter section that also permits dilation. As shown, FIG. 3 shows the first segment 202 having a diameter D1, second segment 204 having diameter D2, and third segment 206 having diameter D3. Where D3 comprises a greater diameter than D2, which is greater than D1. Again, any number of dilator segments can be used. Moreover, variation of the dilator assembly does not require constant diameter sections.

Figure 4A:
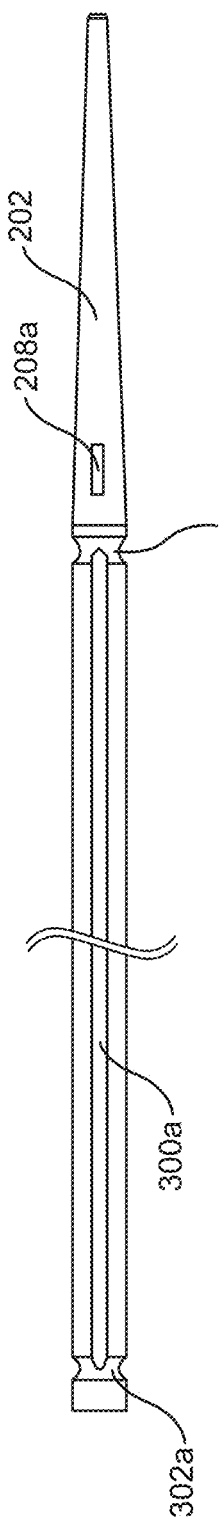
FIG. 4A illustrates a side view of a first dilator of the dilator assembly of FIG. 2.
Figure 4B:
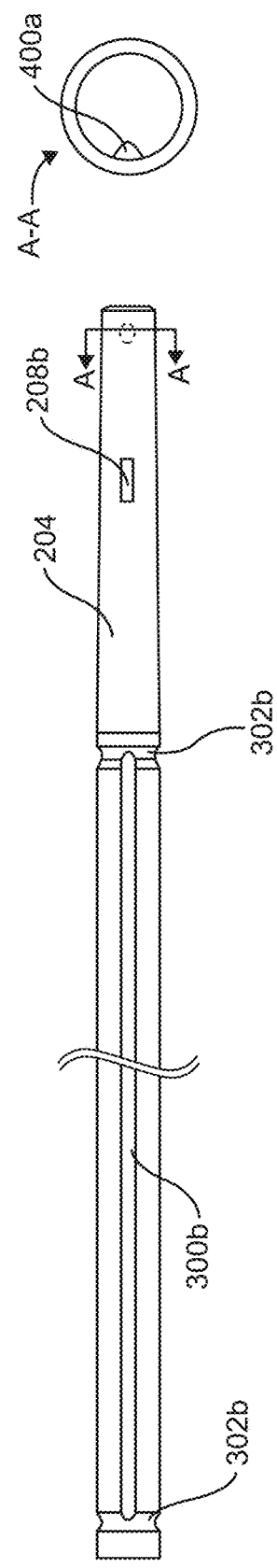
FIG. 4B illustrates a side view of a second dilator of the dilator assembly of FIG. 2.
Figure 4C:
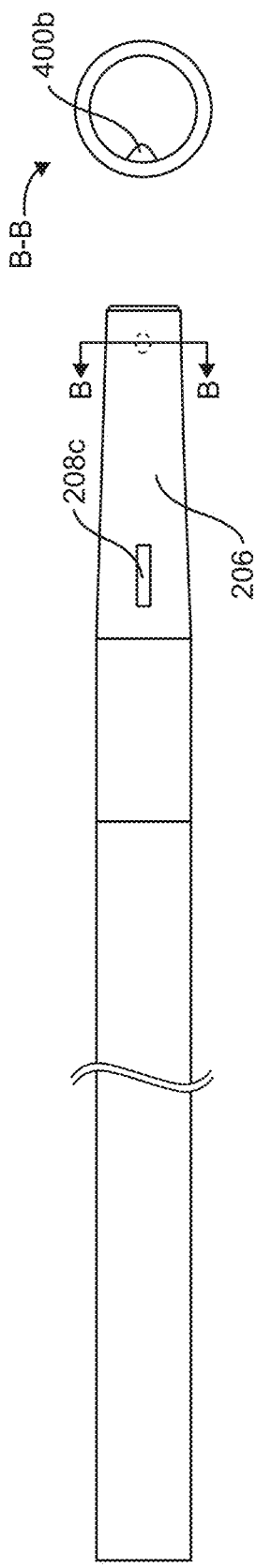
FIG. 4C illustrates a side view of a third dilator of the dilator assembly of FIG. 2.

FIGS. 4A to 4C illustrate respective top views of dilator segments 202, 204, 206. Where FIGS. 4B and 4C also show front sectional views taken along lines AA and BB to illustrate protrusions 400a, 400b on an inner surface of their respective dilator segments. The protrusion 400a, 400b can comprise any shape that nests within the respective grooves to engage the longitudinal groove 300a, 300b or the circumferential groove 302a, 300b of an inner dilator segment. As will be discussed further herein, the protrusion 400a, 300b and the circumferential groove 302a, 302b create a locking mechanism when engaged to lock corresponding dilator segments from relative movement in an axial direction and permit relative movement in a radial direction. The protrusion 400a, 400b and the longitudinal groove 300a, 300b can engage to lock corresponding dilator segments from relative movement in a radial direction and permit relative movement in an axial direction.

Figure 4D:
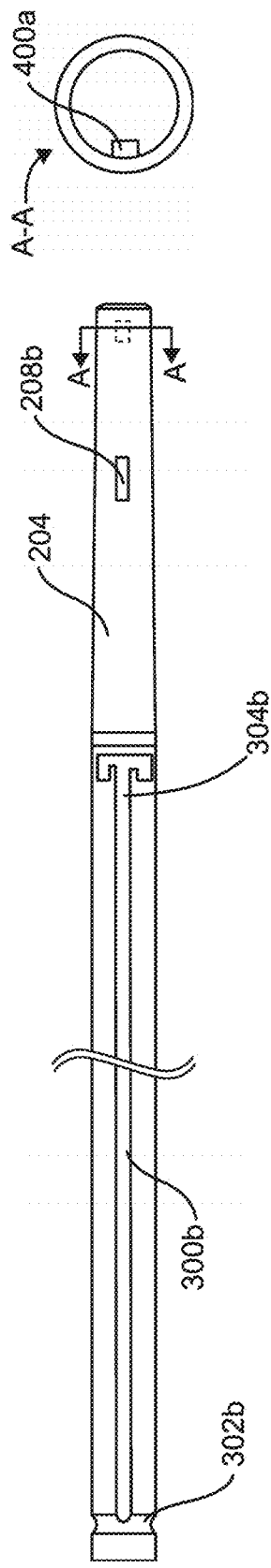
FIGS. 4D to 4F illustrate side views of additional variations of the dilator assembly.
Figure 4E:
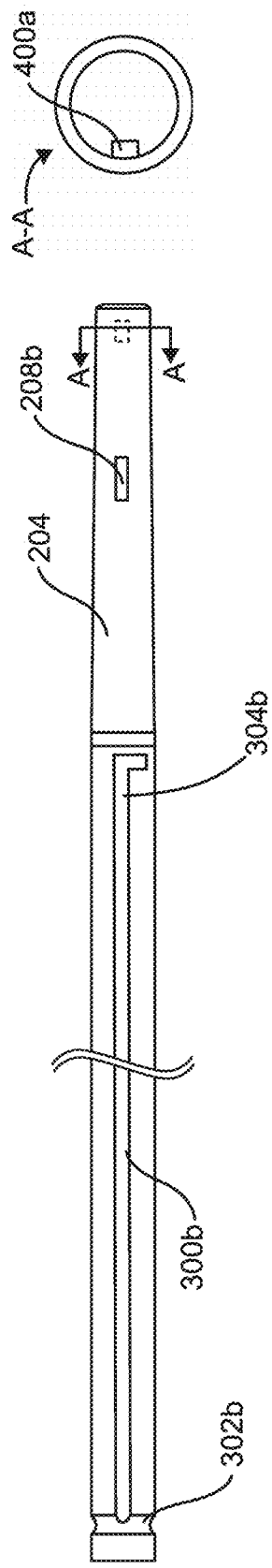
Figure 4F:
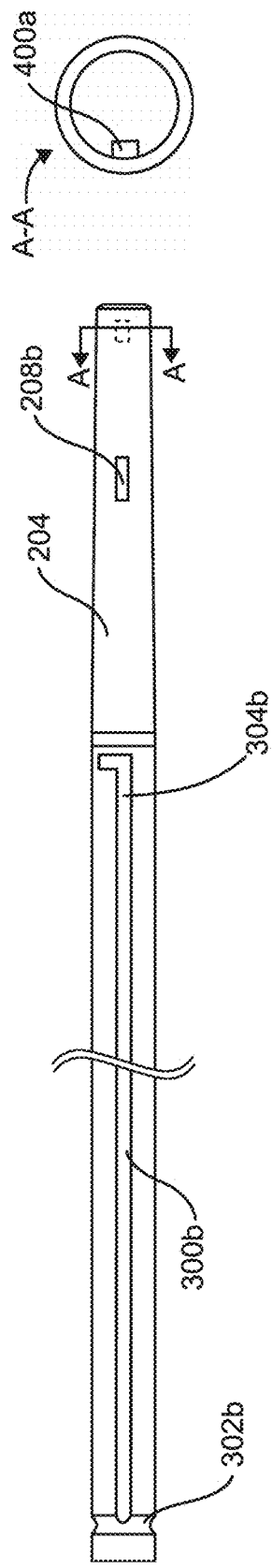

FIGS. 4D to 4F illustrate side views of additional variations of the dilator assembly. Second dilator segment 204 (or any dilator segment) can comprise a longitudinal groove 300b with groove heads 304b towards a distal end of the groove 300b. In the variation of FIG. 4D, the groove head 304b has two radial directions (i.e., T-shaped) and locks with protrusion 400b (or any other protrusion) in either radial direction. When the user withdraws second dilator segment 204 into third dilator segment 206, the protrusion 400b can engage with groove head 304*b* and will lock in either radial direction. Engagement between the protrusion 400*b* and the groove head 304 provides tactile feedback to the user when the dilator segments rotate with respect to each other. The third dilator segment 206 can then be pulled proximally to lock the device. FIGS. 4E and 4F illustrate variations of groove head 304*b* having one radial direction (i.e., L-shaped) such that the protrusion 400*b* can only be locked in one radial direction. In such variations, the protrusions 400*a*, 400*b* can be substantially shaped as a rectangular or square to fit within the groove head 304*b*.

Figure 5A:
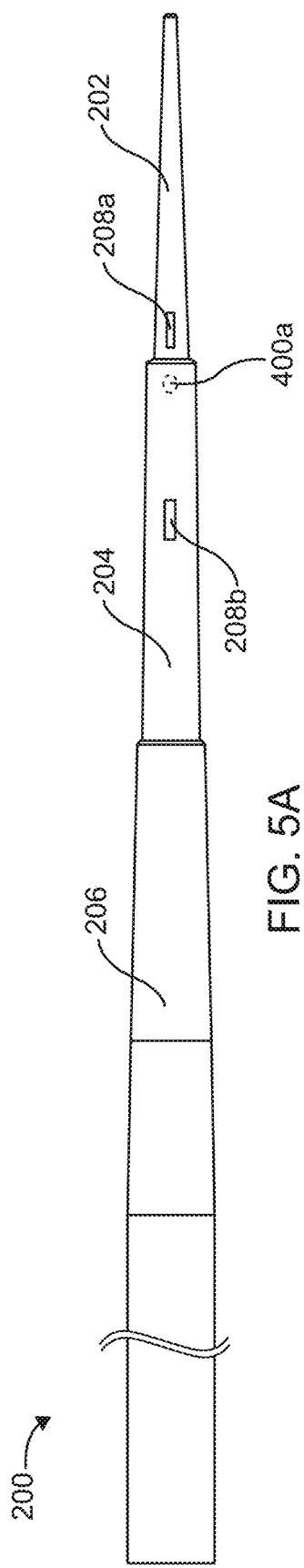
FIGS. 5A to 5C illustrate side views of movement between the first dilator and the second dilator of the dilator assembly of FIG. 2.
Figure 5B:
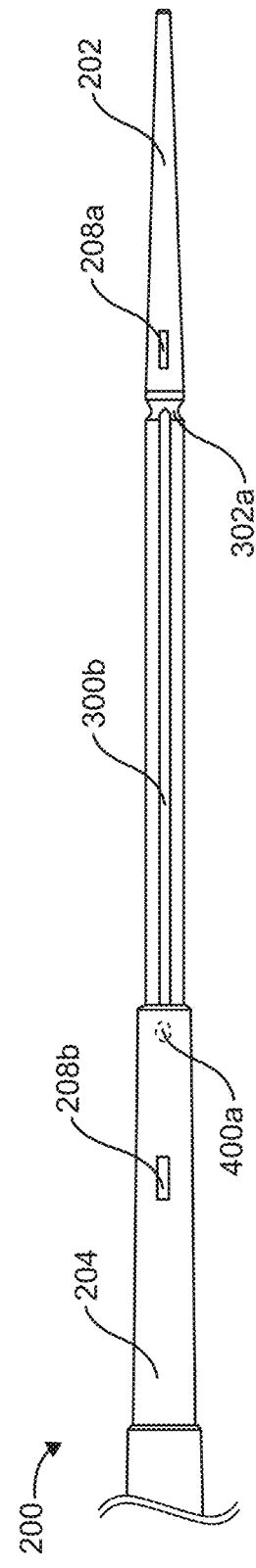
Figure 5C:
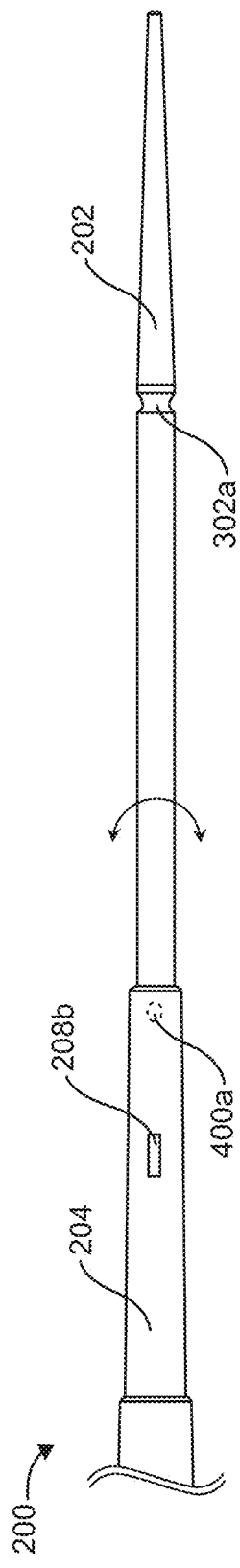

FIGS. 5A to 5C illustrate top views the dilator assembly 200 when the first dilator segment 202 is extended and locked relative to the second dilator segment 204 of the dilator assembly 200. FIG. 5A represents the dilator assembly 200 in a compact configuration, where the alignment marker 208*a* of the first dilator segment 202 is axially oriented with the alignment marker 208*b* of the second dilator segment 204. In one variation, alignment of the alignment markers 208*a*, 208*b* provides visual and/or tactile confirmation that the protrusion 400*a* of the second dilator segment 204 is within the longitudinal groove 300*a* of the first dilator segment 202, which this allows longitudinal movement of the first dilator segment 202 relative to the second dilator segment 204 as seen in FIG. 5B. It is noted that either the first dilator segment 202 can be distally advanced from the dilator assembly 200 and/or the dilator assembly 200 can be proximally withdrawn from the first dilator segment 202.

FIG. 5C illustrates a configuration wherein a length of the first dilator segment 202 can be inserted into the vessel for an initial dilation. As seen in FIG. 5C, the first dilator segment 202 is locked relative to the second dilator segment 204 such that the alignment marker 208*a* of the first dilator segment 202 is no longer aligned with the alignment marker 208*b* of the second dilator segment 204. This signals to the user that the first dilator segment 202 and the second dilator segment 204 cannot be moved relative to each other along the longitudinal axis. It is noted that alternate variations of the assembly 200 can include alignment markers that are in alignment when the assembly 200 components are in a locked configuration. In any case, the alignment components are intended to give a user a visual and/or tactile indication of the state of the assembly 200 components.

In the illustrated example, the user experiences feedback, such as tactile or audible, of the protrusion 400*a* entering the circumferential groove 302*a* and can then rotate of the first dilator segment 202 relative to the longitudinal axis. Alternatively, or in combination, the dilator assembly 200 can be rotated relative to the first dilator segment 202. The relative rotation of the components locks the dilator assembly 200 such that the first dilator segment 202 and the second dilator segment 204 cannot be moved relative to each other along the longitudinal axis. The user can then proceed with dilating the vessel with the first dilator segment 202. It is noted that additional variations of the device will not provide feedback.

To prepare for the next sequential dilation, the user unlocks first dilator segment 202 to move the dilator assembly 200 back to the compact configuration. In the illustrated variation, this is performed by re-aligning the alignment markers 208*a*, 208*b*. This re-alignment provides an indication that the protrusion 400*a* engages the longitudinal groove 300*a*.

FIGS. 5D to 5F illustrate top views of extending the second dilator segment 204 and the third dilator of the dilator assembly 200. FIG. 5D illustrates the alignment marker 208*b* of the second dilator segment 204 aligned with the alignment marker 208*c* of the third dilator segment 206. Again, this alignment provides an indication that the second dilator segment 204 and third dilator segment 206 can be separated. FIG. 5E illustrates an extension of the second dilator segment 204 from the dilator assembly 200. As noted above, the second dilator segment 204 can be axially advanced from the third dilator segment 206 and/or the third dilator assembly 206 can be proximally withdrawn from the second dilator assembly 204.

FIG. 5F locking of the second dilator segment 204. In this variation, the second dilator segment 204 can be rotated with respect to the third dilator segment 206 such that the alignment marker 208*b* of the second dilator segment 204 is no longer aligned with the alignment marker 208*c* of the third dilator segment 206. This signals to the user that the second dilator segment 204 and the third dilator segment 206 are locked relative to each other and prevented from relative axial movement along the longitudinal axis.

When the protrusion 400*b* of the third dilator segment 206 enters the circumferential groove 302*b* of the second dilator segment 204, the user can rotate the second dilator segment 204 about the longitudinal axis. As noted above, variations of the device provide audible or tactile feedback when the protrusion enters the groove. This locks the dilator assembly 200 such that the second dilator segment 204 and the third dilator segment 206 cannot be axially moved relative to each other along the longitudinal axis. The user can then proceed with dilating the vessel with the second dilator segment 204.

FIGS. 6A to 6G illustrate methods of sequentially dilating a vessel with a dilator assembly 200 as described herein. The methods of the present disclosure can include the steps discussed above with respect to FIGS. 1A to 1C, where an incision is first made through the skin 102. A needle assembly 100 is then advanced through the incision and into a target vessel 104. Next, a guidewire 108 advances through the needle assembly 100 into the vessel 104 before the needle assembly 100 is withdrawn from the vessel. Additional incisions can be made as needed.

Figure 6A:
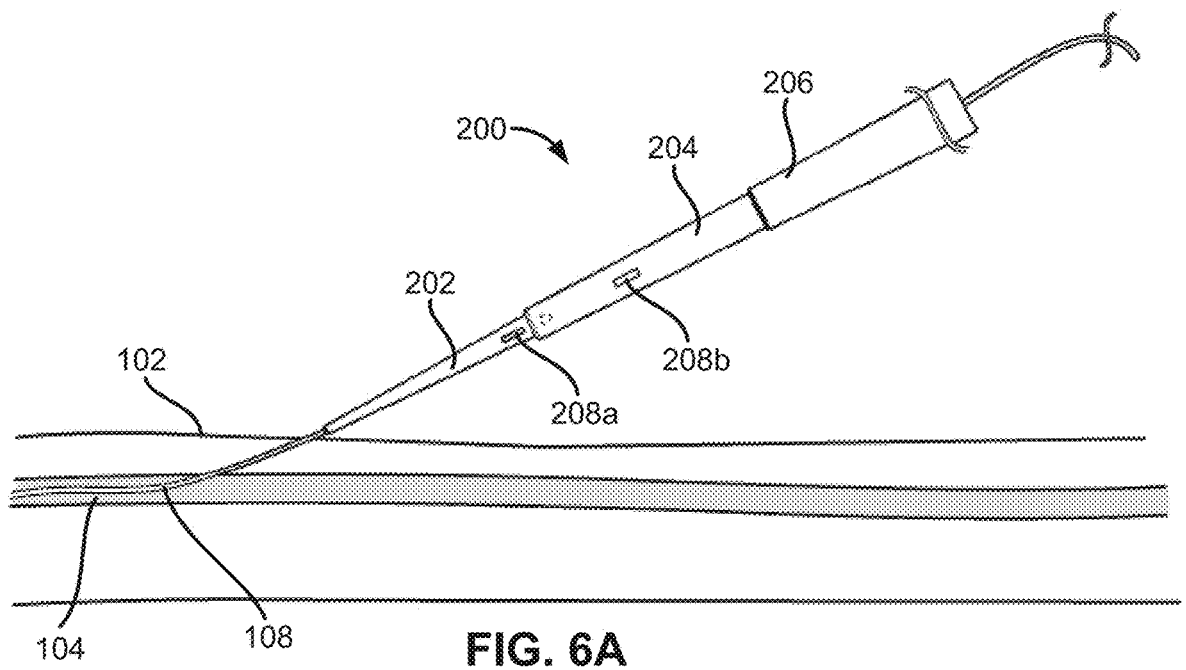
FIGS. 6A to 6G illustrate side views of a method of dilating a vessel with the dilator assembly in accordance with the present invention.

The dilator assembly 200 is advanced over the guidewire 108 at a portion of the guidewire 108 exterior to the incision, as seen in FIG. 6A. In alternate variations, the dilator assembly 200 is inserted into a vessel through an incision with or without a guide sheath. The dilator assembly 200 can be positioned towards the skin 102 while the dilator assembly 200 is in the compact configuration as shown in FIG. 6A, which also shows the alignment marker 208*a* of the first dilator segment 202 aligned with the alignment marker of the second dilator segment 204 before the dilator assembly 200 is advanced through the skin 102.

In the compact configuration, the first dilator segment 202 can be partially nested in the second dilator segment 204, and the second dilator segment 204 can be partially nested in the third dilator segment 206.

Figure 6B:
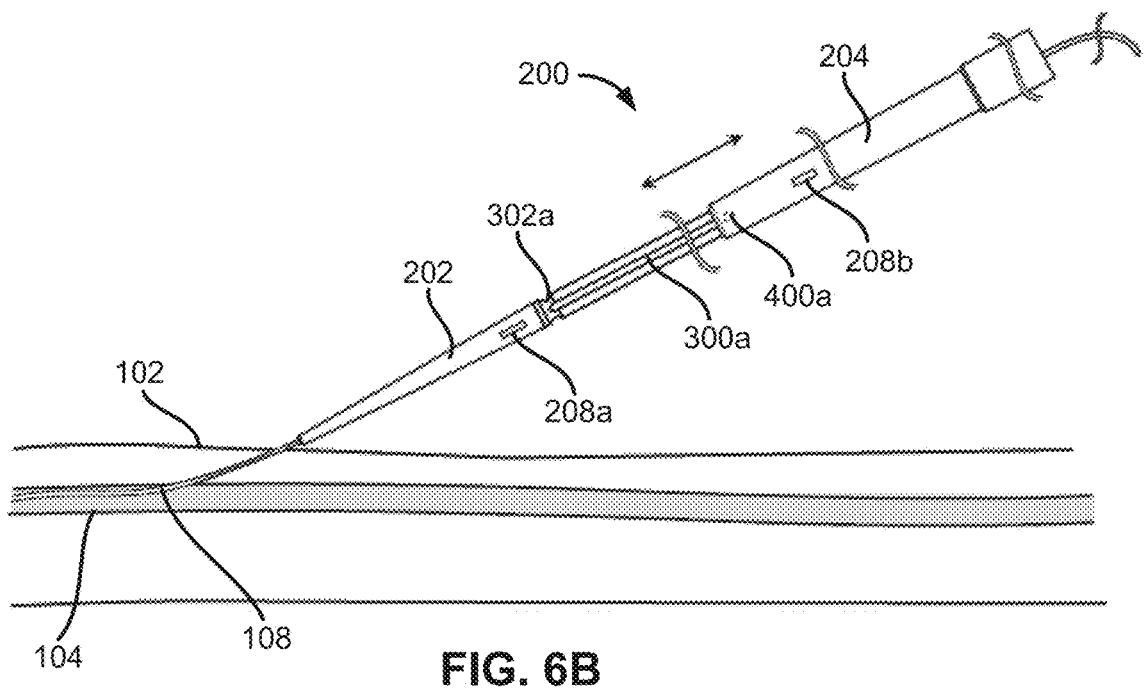
Figure 6C:
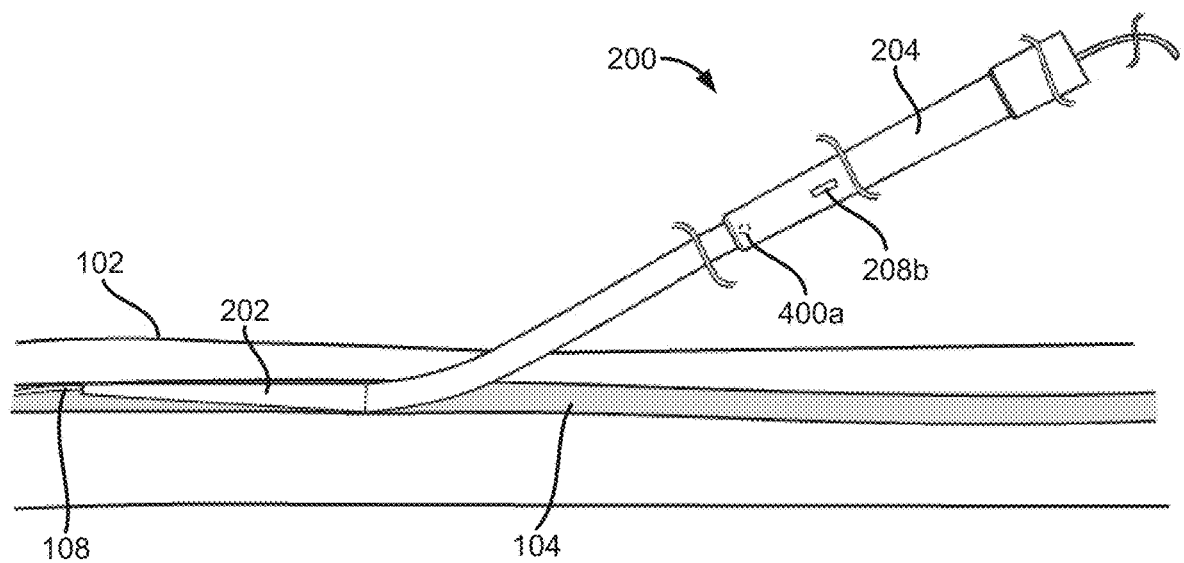

The dilator assembly 200 can be expanded to expose the first dilator segment 202 as shown in FIG. 6B. This expansion can occur before advancement into the vessel 104, as seen in FIG. 6B. Alternatively, the tapered portion of the first dilator segment 202 can be positioned within the skin 102 or vessel 104 before expansion. Next, the first dilator segment 202 or the second dilator segment 204 are rotated to lock the respective segments from moving longitudinally with respect to each other in FIG. 6C. Again, a user can verify that the dilator assembly 200 is in a longitudinally locked configuration using the alignment marker 208*a*, 208*b*. The dilator assembly 200 can then be advanced to perform a first dilation of the vessel 104 with the first dilator segment 202.

Figure 6D:
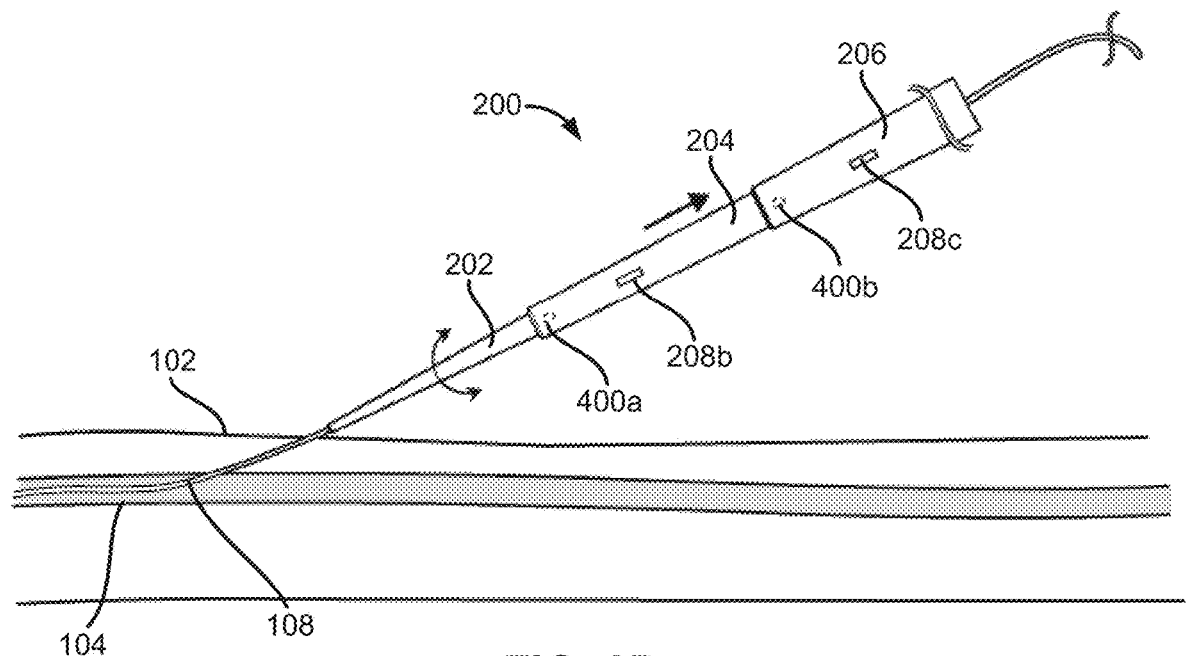
Figure 6E:
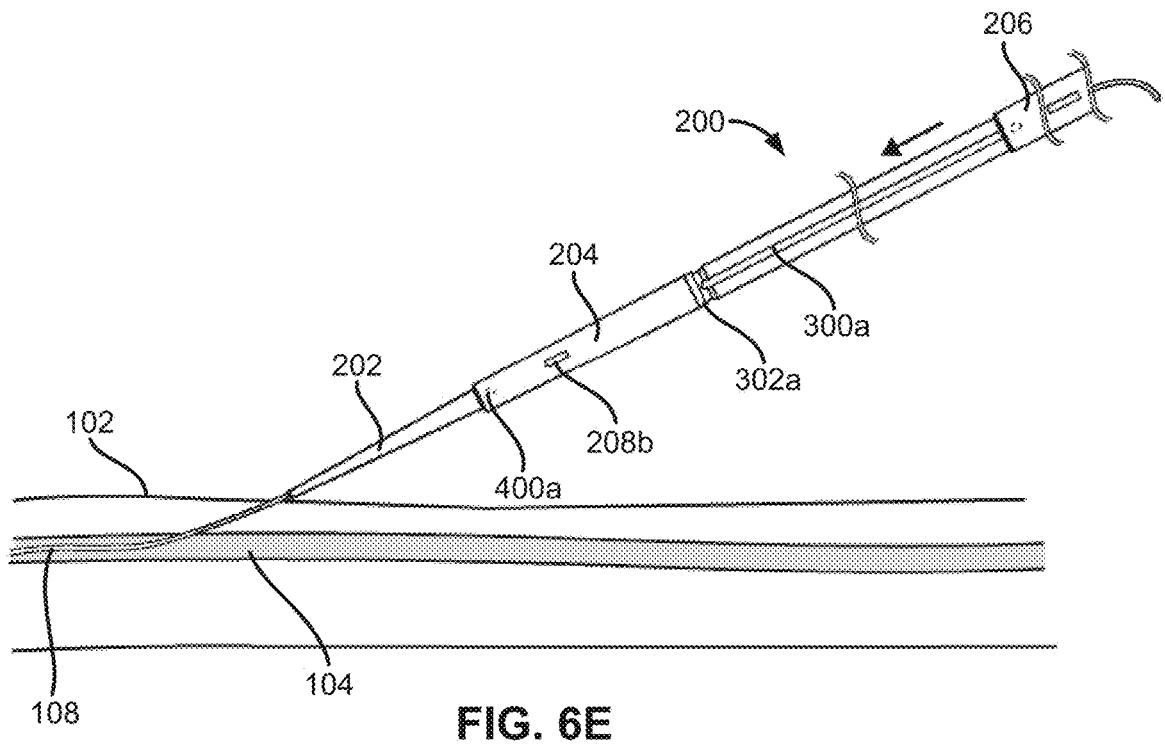
Figure 6F:
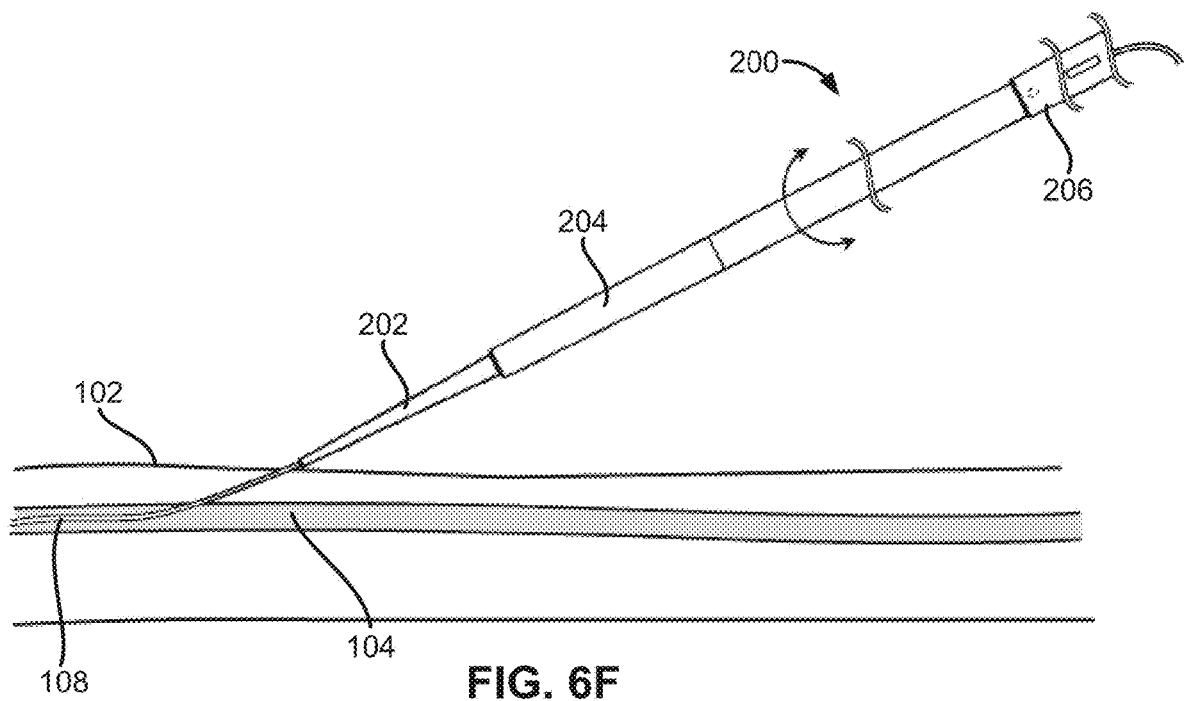
Figure 6G:
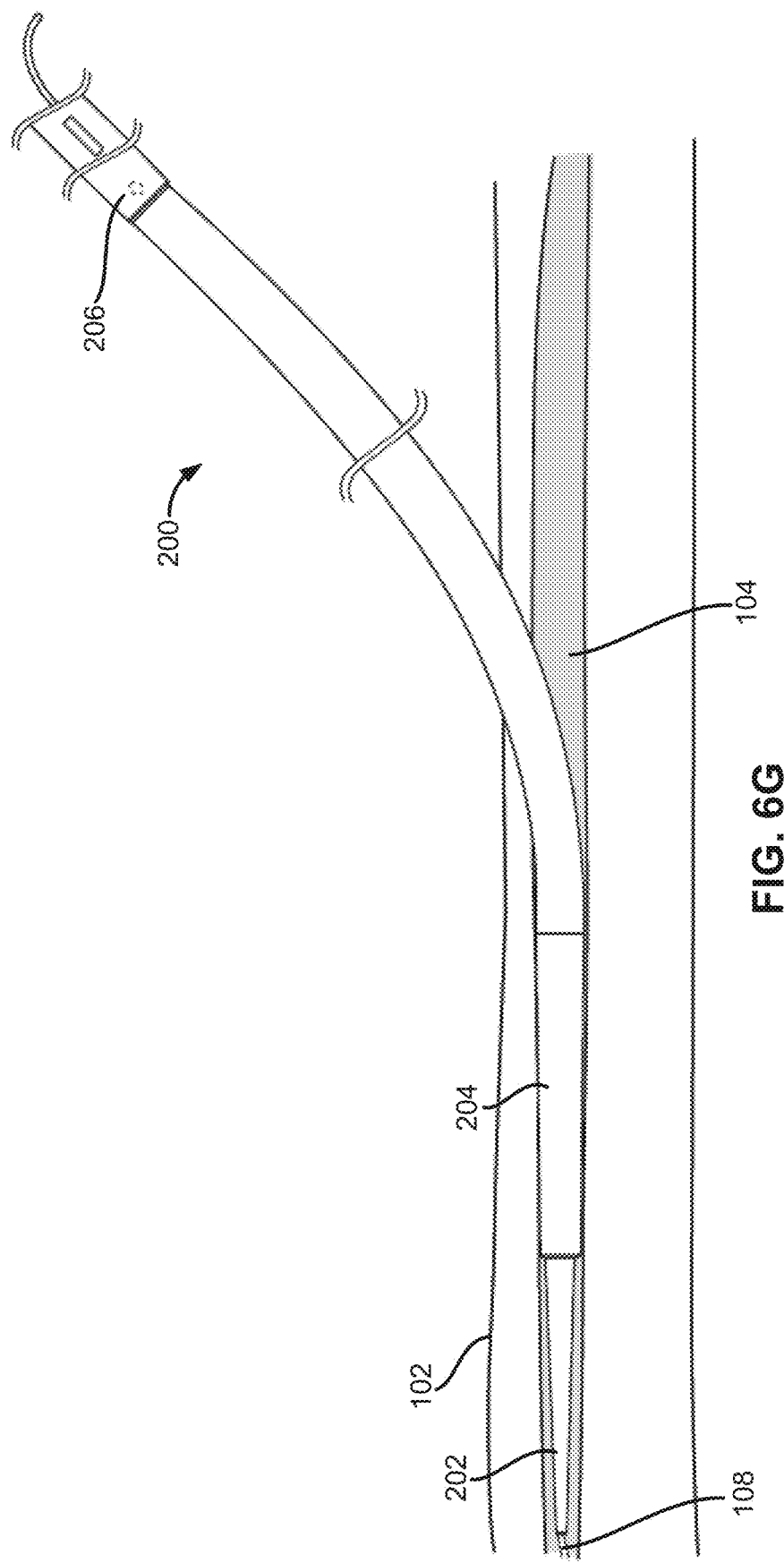

FIG. 6D illustrates the first dilator segment 202 after it has been withdrawn from the vessel 104 and positioned back into the dilator assembly 200. Next, as shown in FIG. 6E, the second dilator segment 204 can be expanded from the third dilator segment 206. The first dilator segment 202 can remain partially extended from and coupled to the second dilator segment 204 while the second dilator segment 204 is extended from the dilator assembly 200. The second dilator segment 204 is then locked to the third dilator segment 206 as shown in FIG. 6F. Optionally, the alignment marker 208b of the second dilator segment 204 and the alignment marker 208c of the third dilator segment 206 can be used to confirm the locked configuration. The dilator assembly 200 can then be advanced to perform a second dilation with the second dilator segment 204, as seen in FIG. 6G.

Although not illustrated, the dilator assembly positioned in the compact configuration for further dilation by the third dilator segment 206. Doing so results in three sequentially sized dilations from a single dilator assembly 200 that remains on the wire during each dilation. Again, any number of dilator segments greater than two can be used in the sequential dilator assembly. As noted above, this eliminates the need for a caregiver to remove different sized dilators from the guidewire.

The dilator assemblies disclosed herein address problems with the conventional multiple sequential dilators by reducing the risk of infection from guidewire mishandling and also reduces the time of the procedure. As discussed above, the dilator assembly 200 performs multiple dilations while remaining on a guidewire. Since any dilation of an opening into a vessel increases blood flow exiting the site and vessel, during conventional sequential dilation, a caregiver must put pressure on the site while removing a dilator from the guidewire and repositioning the next dilator. Use of the sequential dilator assembly described herein reduces procedure time and prevents excessive handling and/or repositioning of the guidewire.

Figure 7A:
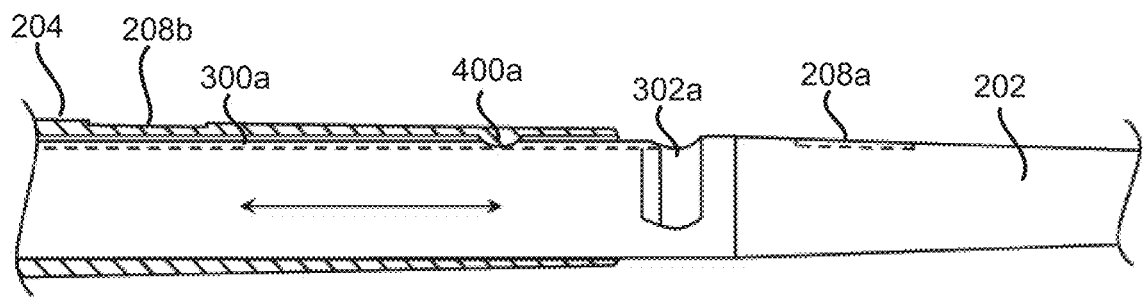
FIGS. 7A and 7B illustrate close-up side views of the locking mechanism of the first dilator and the second dilator.
Figure 7B:
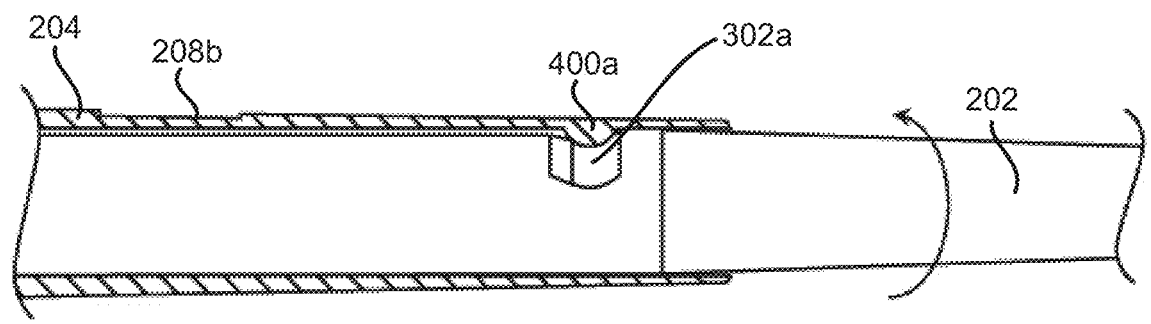

FIGS. 7A and 7B illustrate magnified partial cross-sectional side views of one variation of a locking mechanism of the first dilator segment 202 and the second dilator segment 204. The first dilator segment 202 can move longitudinally with respect to the second dilator segment 204 when the protrusion of the second dilator segment 204 is engaged with the longitudinal groove of the first dilator segment 202, as seen in FIG. 7A.

As seen in FIG. 7B, when protrusion 400a is engaged with the circumferential groove 302a of the first dilator segment 202, the first dilator segment 202 can rotate radially with respect to the second dilator segment 204. The first dilator segment 202 can be locked from moving longitudinally with respect to the second dilator segment 204 in this configuration.

It should be noted that the configuration of the locking assembly disclosed above is for illustrative purposes only. Any number of locking assemblies can be used as long as the dilator segments can function to dilate the vessel. Moreover, the groove disclosed above can extend spirally along a respective dilator segment. Alternatively, or in combination, more than one groove and protrusion can be used in variations of the device.

The proximal or distal circumferential grooves 302a, 302b can be used along with the protrusion 400a, 400b to vary the length of the entire dilator assembly 200.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps or operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit, or scope of the present invention.

Methods recited herein may be carried out in any order of the recited events that is logically possible, as well as the recited order of events. Moreover, additional steps or operations may be provided, or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to +0.1%, +1%, +5%, or +10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

It will be understood by one of ordinary skill in the art that the various methods disclosed herein may be embodied in a non-transitory readable medium, machine-readable medium, and/or a machine accessible medium comprising instructions compatible, readable, and/or executable by a processor or server processor of a machine, device, or computing device. The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A method for sequentially dilating a vessel, where a guidewire extends into the vessel through a tissue opening in a tissue surface, the method comprising:

advancing a dilator assembly over a portion of the guidewire that is exterior to the tissue opening;

positioning the dilator assembly over the guidewire and towards the tissue surface while the dilator assembly is in a compact configuration;

extending a first dilator segment from the dilator assembly;

advancing at least the first dilator segment into the tissue opening to dilate the vessel while the first dilator segment remains extended from the dilator assembly;

withdrawing the first dilator segment from the tissue opening and retracting the first dilator segment into the dilator assembly;

extending a second dilator segment from the dilator assembly, where the first dilator segment remains coupled to the second dilator segment and partially extends from the second dilator segment;

advancing the first dilator segment and the second dilator segment into the tissue opening to further sequentially dilate the vessel while the second dilator segment remains extended from the dilator assembly;

withdrawing the first dilator segment and the second dilator segment from the tissue opening and retracting the second dilator segment into the dilator assembly; and withdrawing the dilator assembly from the guidewire.

2. The method of claim 1, further comprising locking the dilator assembly via a locking mechanism, wherein the locking mechanism comprises a protrusion on an inner surface of the second dilator segment and a groove on an outer surface of the first dilator segment, wherein rotating the second dilator segment with respect to the first dilator segment engages the protrusion with the groove to lock the dilator assembly.

3. The method of claim 2, further comprising a plurality of grooves radially spaced apart on the outer surface of the first dilator segment, wherein the protrusion is configured to engage with any of the plurality of grooves.

4. The method of claim 1, wherein the first dilator segment fully extends from the second dilator segment.

5. The method of claim 1, further comprising extending a third dilator segment from the dilator assembly, where the first dilator segment and the second dilator segment remains coupled to the third dilator segment and partially extend from the third dilator segment;

advancing the third dilator segment, the second dilator segment, and the first dilator segment into the tissue opening to further sequentially dilate the vessel while the third dilator segment remains extended from the dilator assembly; and withdrawing the first dilator segment, the second dilator segment, and the third dilator segment from the tissue opening and retracting the third dilator segment into the dilator assembly.

6. The method of claim 5, wherein the second dilator segment fully extends from the third dilator segment.

7. The method of claim 5, further comprising a locking mechanism, wherein the locking mechanism comprises a protrusion on an inner surface of the third dilator segment and a groove on an outer surface of the second dilator segment, wherein rotating the third dilator segment with respect to the second dilator segment engages the protrusion of the third dilator segment with the groove of the second dilator segment to lock the dilator assembly.

8. The method of claim 1, wherein the first dilator segment comprises a first alignment marker, the second dilator segment comprises a second alignment marker, wherein the first alignment marker and the second alignment marker are longitudinally aligned when the first dilator segment is axially moveable relative to the second dilator segment.

9. The method of claim 8, wherein the first alignment marker and the second alignment marker are longitudinally misaligned when the first dilator segment is axially locked relative to the second dilator segment.

10. The method of claim 8, wherein the first alignment marker and the second alignment marker are longitudinally misaligned when the first dilator segment is rotatable relative to the second dilator segment.

* * * * *